United States Patent
Yehezkely et al.

(10) Patent No.: US 12,374,444 B2
(45) Date of Patent: Jul. 29, 2025

(54) CREATING A SYNTHETIC MEDICAL IMAGE

(71) Applicant: KONINKLIJKE PHILIPS N.V., Eindhoven (NL)

(72) Inventors: Shelly Theodora Yehezkely, Haifa (IL); Yossef Kam, Haifa (IL); Mooly Cohen, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 26 days.

(21) Appl. No.: 17/918,163

(22) PCT Filed: Apr. 7, 2021

(86) PCT No.: PCT/EP2021/058980
§ 371 (c)(1),
(2) Date: Oct. 11, 2022

(87) PCT Pub. No.: WO2021/209287
PCT Pub. Date: Oct. 21, 2021

(65) Prior Publication Data
US 2023/0132504 A1    May 4, 2023

(30) Foreign Application Priority Data
Apr. 14, 2020 (EP) .................... 20169281

(51) Int. Cl.
*G09G 5/00* (2006.01)
*G06T 7/11* (2017.01)
(Continued)

(52) U.S. Cl.
CPC .............. *G16H 30/40* (2018.01); *G06T 7/11* (2017.01); *G06T 7/337* (2017.01); *G06T 11/60* (2013.01);
(Continued)

(58) Field of Classification Search
CPC .... G09G 5/14; G09G 2340/125; G09G 5/395; G09G 2349/10; G09G 2340/12;
(Continued)

(56) References Cited

U.S. PATENT DOCUMENTS 9,330,444 B2    5/2016    Wang
10,769,791 B2   9/2020    Song
(Continued)

FOREIGN PATENT DOCUMENTS

| | | |
|---|---|---|
| JP | 2014174174 A | 9/2014 |
| JP | 2016527942 A | 9/2016 |
| WO | 2005059831 A1 | 6/2005 |

OTHER PUBLICATIONS

Nalepa et al., "Data Augmentation for Brain-Tumor Segmentation: A Review", Frontiers in Computational Neuroscience, vol. 13, Dec. 11, 2019, pp. 1-18.
(Continued)

*Primary Examiner* — Gordon G Liu

(57) ABSTRACT

An apparatus for creating a synthetic medical image comprises a memory comprising instruction data representing a set f instructions and a processor configured to communicate with the memory and to execute the set of instructions. The set of instructions, when executed by the processor, cause the processor to obtain first and second medical images, determine an elastic deformation that can be used to register the first medical image onto the second medical image, and create the synthetic medical image by weighting the determined elastic deformation and applying the weighted elastic deformation to a portion of the first medical image.

15 Claims, 3 Drawing Sheets

(51) Int. Cl.
*G06T 7/33* (2017.01)
*G06T 11/60* (2006.01)
*G16H 30/40* (2018.01)
*G16H 30/20* (2018.01)

(52) U.S. Cl.
CPC ..... *G06T 2200/04* (2013.01); *G06T 2207/20021* (2013.01); *G06T 2207/20104* (2013.01); *G06T 2207/30004* (2013.01); *G16H 30/20* (2018.01)

(58) Field of Classification Search
CPC .......... G16H 30/40; G16H 30/20; G06T 7/11; G06T 7/337; G06T 11/60; G06T 2200/04; G06T 2207/20021; G06T 2207/20104; G06T 2207/30004
USPC ........................................................ 345/634
See application file for complete search history.

(56) References Cited

U.S. PATENT DOCUMENTS

| | | |
|---|---|---|
| 12,048,574 B2 | 7/2024 | Sapiro |
| 2005/0146536 A1 | 7/2005 | Battle |
| 2010/0172567 A1* | 7/2010 | Prokoski ................ A61B 5/418 |
| | | 348/47 |
| 2011/0235884 A1 | 9/2011 | Schreibmann |
| 2012/0041446 A1* | 2/2012 | Wong ................ A61F 2/30756 |
| | | 606/86 R |
| 2014/0081122 A1 | 3/2014 | Schmidt |
| 2018/0360313 A1 | 12/2018 | Zhang |
| 2019/0362522 A1* | 11/2019 | Han ..................... A61N 5/1039 |
| 2020/0090349 A1 | 3/2020 | Chen et al. |
| 2020/0121951 A1* | 4/2020 | Morgas ................ A61N 5/1067 |

OTHER PUBLICATIONS

Yi Xin et al., "Generative adversarial network in medical imaging: A review", Medical Image Analysis, Oxford University, Press, Oxford, GB, vol. 58, Aug. 31, 2019, XP085878766, ISSN: 1361-8415, DOI: 10.2016/J.Media.2019.101552 [retrieved on Aug. 31, 2019] the whole document.
International Search Report and Written Opinion of PCT/EP2021/058980, dated Apr. 7, 2021.

* cited by examiner

CREATING A SYNTHETIC MEDICAL IMAGE

CROSS-REFERENCE TO PRIOR APPLICATIONS

This application is the U.S. National Phase application under 35 U.S.C. § 371 of International Application No. PCT/EP2021/058980, filed on Apr. 7, 2021, which claims the benefit of European Patent Application No. 20169281.1, filed on Apr. 14, 2020. These applications are hereby incorporated by reference herein.

FIELD OF THE INVENTION

Embodiments herein relate to medical imaging. Particularly but non-exclusively, embodiments herein relate to creating synthetic medical images.

BACKGROUND OF THE INVENTION

This disclosure lies in the area of medical imaging. Medical images can be scarce, expensive, and sometimes difficult to obtain. Examples of medical images include computed tomography (CT) images (for example, from a CT scan) such as a C-arm CT image, a spectral CT image or a phase contrast CT Image, an x-ray image (for example, from an x-ray scan), a magnetic resonance (MR) image (for example, from an MR scan), an ultrasound (US) image (for example, from an ultrasound scan), fluoroscopy images, and nuclear medicine images.

US2020/00900349A1 shows a medical image diagnostic apparatus that performs image registration between medical image data. It discloses pre-registration between medical data on a display scale of a first specified value and then performs formal image registration on more than one display scales of a second specified value. The second specified value is smaller than the first specified value. It discloses partial registration for the image through a matching method using a relative microscopic structure. It performs finer registration on the display scales of the second specified values which are smaller than the first specified value under the consideration of the relative macroscopic image information in the image, thereby achieving fine and global image registration.

US2005/0146536A1 discloses a statistically-based image blending method for pasting a plurality of digital sub-images together into a single final past image. It discloses to blend pixel intensities of at least two digital sub-images together to create a single pasted image thereof.

In the scientific paper "Generative adversarial network in medical imaging: A review" by Xin Yi, Ekta Walia and Paul Baby, disclose the use of a Generative Adversarial Networks (GAN) for creating training data.

It is an object of embodiments herein to improve on the availability of medical images.

SUMMARY OF THE INVENTION

As described above medical images can be scarce, difficult and/or expensive to obtain. Large corpuses of medical imagery are needed to develop (train and test) model classifiers in this field, such as machine learning models for improved image reading output. One way to overcome such scarcities of medical image data is to use synthetic image data. However classical methods for generating synthetic data can be based on phantoms (e.g. physical or synthetic models specially designed to evaluate, analyze, and/or tune the performance of an imaging device) which don't necessarily represent real clinical data.

It is an object of some embodiments herein to improve upon this situation by providing systems and methods for creating synthetic medical images.

Thus, according to a first aspect herein, there is an apparatus for creating a synthetic medical image. The apparatus comprises a memory comprising instruction data representing a set of instructions, and a processor configured to communicate with the memory and to execute the set of instructions. The set of instructions, when executed by the processor, cause the processor to obtain first and second medical images, determine an elastic deformation that can be used to register the first medical image onto the second medical image, and create the synthetic medical image by weighting the determined elastic deformation and applying the weighted elastic deformation to a portion of the first medical image.

Thus in this manner the apparatus can create synthetic medical images from other (e.g. real) medical images by extrapolating between them. The resulting synthetic images may be more likely to be representative of real medical images, compared to, for example, images produced from models. This is because the distortion or extrapolation is made based on variability that is actually seen in the human population (e.g. the type of deformation is based on real observed differences rather than a purely hypothetical differences). Thus the shapes of anatomical features in the resulting synthetic image are likely to fall within the range of shapes seen in real populations.

According to a second aspect there is a method of creating a synthetic medical image. The method comprises obtaining first and second medical images, determining an elastic deformation that can be used to register the first medical image onto the second medical image, and creating the synthetic medical image by weighting the determined elastic deformation and applying the weighted elastic deformation to a portion of the first medical image.

According to a third aspect there is a computer program product comprising a computer readable medium, the computer readable medium having computer readable code embodied therein, the computer readable code being configured such that, on execution by a suitable computer or processor, the computer or processor is caused to perform the method of the second aspect.

BRIEF DESCRIPTION OF THE DRAWINGS

For a better understanding and to show more clearly how embodiments herein may be carried into effect, reference will now be made, by way of example only, to the accompanying drawings, in which.

DETAILED DESCRIPTION OF EMBODIMENTS

Figure 1:
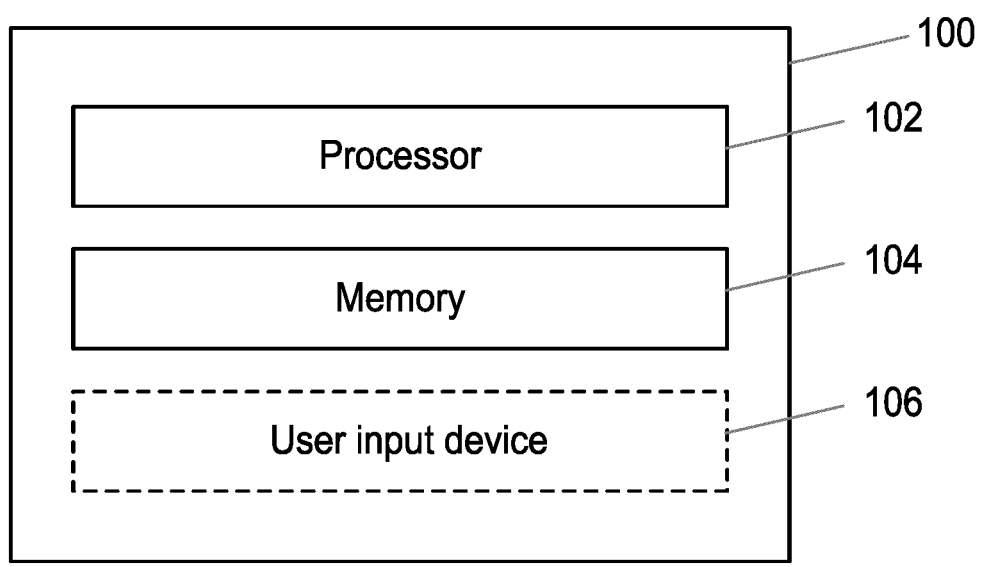
FIG. 1. illustrates an apparatus according to some embodiments herein.

FIG. 1 illustrates an apparatus for creating a synthetic image according to some embodiments herein. The apparatus may form part of (e.g. be comprised in) a computer system e.g.

such as a laptop, desktop computer or other device. In some embodiments, the apparatus 100 may form part of the cloud/a distributed computing arrangement.

The apparatus comprises a memory 104 comprising instruction data representing a set of instructions and a processor 102 configured to communicate with the memory and to execute the set of instructions. Generally, the set of instructions, when executed by the processor, may cause the processor to perform any of the embodiments of the methods 200 or 300 as described below.

More specifically, the set of instructions, when executed by the processor, cause the processor to: i) obtain first and second medical images, ii) determine an elastic deformation that can be used to register the first medical image onto the second medical image, and iii) create the synthetic medical image by weighting the determined elastic deformation and applying the weighted elastic deformation to a portion of the first medical image.

The processor 102 can comprise one or more processors, processing units, multi-core processors or modules that are configured or programmed to control the apparatus 100 in the manner described herein. In particular implementations, the processor 102 can comprise a plurality of software and/or hardware modules that are each configured to perform, or are for performing, individual or multiple steps of the method described herein. The processor 102 can comprise one or more processors, processing units, multi-core processors and/or modules that are configured or programmed to control the apparatus 100 in the manner described herein. In some implementations, for example, the processor 102 may comprise a plurality of (for example, interoperated) processors, processing units, multi-core processors and/or modules configured for distributed processing. It will be appreciated by a person skilled in the art that such processors, processing units, multi-core processors and/or modules may be located in different locations and may perform different steps and/or different parts of a single step of the method described herein.

The memory 104 is configured to store program code that can be executed by the processor 102 to perform the method described herein. Alternatively or in addition, one or more memories 104 may be external to (i.e. separate to or remote from) the apparatus 100. For example, one or more memories 104 may be part of another device. Memory 104 can be used to store, for example, the first and second medical images, the created synthetic image, user inputs received from a user, and/or any other information and/or data received, calculated or determined by the processor 102 of the apparatus 100 or from any interfaces, memories or devices that are external to the apparatus 100. The processor 102 may be configured to control the memory 104 to store the first and second medical images, the created synthetic image, and/or the any other information described herein.

In some embodiments, the memory 104 may comprise a plurality of sub-memories, each sub-memory being capable of storing a piece of instruction data. For example, at least one sub-memory may store instruction data representing at least one instruction of the set of instructions, while at least one other sub-memory may store instruction data representing at least one other instruction of the set of instructions.

The apparatus may further comprise a user input device 106, such as a keyboard, mouse or other input device that enables a user to interact with the apparatus, for example, to provide the first and/or second user inputs described below. In other embodiments, such a user input device 106 may be remote from the apparatus 100 and the apparatus 100 may receive any user input from a remote user input device 106 using electronic signals, e.g. via a wired or wireless internet connection.

It will be appreciated that FIG. 1 only shows the components required to illustrate this aspect of the disclosure and, in a practical implementation, the apparatus 100 may comprise additional components to those shown. For example, the apparatus 100 may comprise a battery or other power supply for powering the apparatus 100 or means for connecting the apparatus 100 to a mains power supply.

In more detail, the first medical image may comprise a medical image of a human or animal subject e.g. a "real" human or animal subject. The first medical image may have been obtained, for example, during a medical examination, or scan. The first medical image may comprise a stock image from a database of medical images.

Alternatively, the first medical image may comprise a synthetic medical image (in such an example, the methods described herein may thus be used to create further synthetic images from initial first and second synthetic images).

The second medical image may comprise an image obtained in the same or different manner to the first medical image. For example, the second medical image may have been obtained, for example, during a medical examination, or scan. The second medical image may comprise a stock image from a database of medical images. The second medical image may alternatively comprise a synthetic medical image.

The second medical image may comprise a medical image of the same type of subject (e.g. human or animal) as the first medical image. The second medical image may comprise a different subject to the first medical image, for example, the first medical image may comprise an image of a first person (e.g. first patient or subject) and the second medical image may comprise an image of a second person (e.g. second patient or subject).

The first and second medical images will generally comprise common or overlapping features (such as common anatomical features). Generally, the first and second medical images may comprise a common landmark or landmarks that enable the first medical image to be registered to the second medical image (in step ii) as described below). For example, both the first and second medical images may comprise images of the same anatomical feature. Examples of anatomical features include, but are not limited to a lung, a heart, a ventricle in a heart, a brain, a fetus, etc.

Generally, for example, the first medical image may thus comprise a particular anatomical feature of a first person and the second medical image may comprise the same anatomical feature of a second person.

The first and second medical images may comprise medical images of any imaging modality, including but not limited to: a computed tomography (CT) image (for example, from a CT scan) such as a C-arm CT image, a spectral CT image or a phase contrast CT Image, an x-ray image (for example, from an x-ray scan), a magnetic resonance (MR) image (for example, from an MR scan), an ultrasound (US) image (for example, from an ultrasound scan), fluoroscopy images, nuclear medicine images, or any other type of medical images.

In some embodiments, the first medical image may comprise an image of the same modality as the second medical image. E.g. the first and second medical images may both be x-ray images, or MRI images, etc.

The first and second medical images may comprise two dimensional images. In other embodiments, the first and second medical images may comprise three-dimensional images. In some embodiments, the first and second medical images may comprise two-dimensional slices through respective three-dimensional image volumes. The first and second medical images will generally comprise a plurality (or set) of image components. For example, in embodiments where the first and second medical images comprise two-dimensional images, the image components may comprise pixels. For example, in embodiments where the first and second medical images comprise three-dimensional images, the image components may comprise voxels.

Turning back to the apparatus 100, in block i), in some embodiments, the first and/or second medical images may be obtained, for example, from a database of images. The skilled person will appreciate that the first and second medical images may also be obtained through other means, for example in real-time as a scan is performed, or via the internet.

In some embodiments, the apparatus 100 may be configured to receive a user input (referred to herein as the "third user input") comprising an indication of one or more demographic criteria (e.g. criteria relating to the type of synthetic image that is required). The third user input may be obtained, for example, from a user input device such as the user input device 106 in FIG. 1. Examples of demographic criteria include, but are not limited to an age, sex or ethnicity.

In some embodiments, the apparatus may be configured to select the first and/or second medical image from a database of images, based on the demographics of respective human subjects in the images in the database of images and the demographic criteria.

For example, the user may provide a user input indicating that they would like to generate a synthetic image of a subject with a particular age and/or gender. In block i), the processor may thus be caused to select first and second medical images from subjects of matching age and gender, from the database of medical images. In this manner, the user is able to generate synthetic medical images of different demographic groups.

In block ii) the processor is caused to determine an elastic (e.g. non-rigid) deformation that can be used to register the first medical image onto the second medical image. The skilled person will be familiar with methods of performing image registration and methods for determining an elastic deformation that can be used to register the first medical image onto the second medical image. The elastic deformation may comprise translational, rotational, and/or non-linear elements (e.g. the elastic deformation may generally warp the first medical image). The elastic deformation may thus be described as a "deformation field". Example methods of image registration are described, for example, in the paper by T. Netsch et al. entitled: "*Towards Real-Time Multi-Modality* 3*-D Medical Image Registration.*"; International Conference on Computer Vision, 2001. The skilled person will appreciate that these are examples, however, and that any method suitable for determining an elastic deformation to register the first medical image onto the second medical image may be used, examples include landmark registration.

Generally, the elastic deformation may be determined based on landmarks across the whole of the first medical image, or a based on a portion of the first medical image. In other words, the elastic deformation field may be determined on a portion of the first medical image, and does not necessarily need to be determined across the entirety of the first medical image.

In block iii) the processor is then caused to create the synthetic medical image by weighting (e.g. applying a weighting to) the determined elastic deformation and applying the weighted elastic deformation to a portion of the first medical image. In other words, a portion of the first medical image is selected and some proportion of the determined elastic deformation is applied to this portion in order to create the synthetic image. As such the first medical image is deformed or changed so as to create an image having features that are geometrically between those in the first and second medical images.

The weighting may comprise any value, w, in the range $0<w<1$. E.g. any percentage or proportion of the full elastic deformation.

The amount of deformation may be configurable. For example, in some embodiments the weighting may be user configurable, e.g. the apparatus 100 may be configured to receive a second user input (e.g. from a user input device such as user input device 106) comprising a value for the weighting. In this manner, the user may be able to specify how distorted the synthetic image should be compared to the first medical image.

In some embodiments, the set of instructions, when executed by the processor, further cause the processor to: repeat block iii) for a plurality of different weightings to create a plurality of different synthetic images. For example, the second user input may comprise a plurality of different weightings. In this manner a plurality of different synthetic images may be created in an efficient manner.

As noted above, the synthetic image is created by weighting the determined elastic deformation and applying the weighted elastic deformation to a portion of the first medical image. The weighted elastic deformation may thus be applied to the full first medical image, or a portion of the first medical image. Thus in some embodiments, the processor being caused to create the synthetic image comprises the processor being caused to apply the weighted elastic deformation to the entire first medical image, such that the created synthetic image is the same size as the first medical image. In other embodiments, the synthetic image may be created by applying the weighted elastic deformation to a subset of image elements of the first medical image, the resulting synthetic image comprising just said subset of image elements, e.g. the synthetic image may comprise a portion selected from the full first medical image.

In some embodiments, the apparatus may be configured to receive a first user input (e.g. from a first user input device 106) indicating a region of interest and the set of instructions, when executed by the processor, cause the processor to perform blocks i), ii) and iii) responsive to receiving the first user input.

The first user input may comprise a set of coordinates that demarcate the region of interest. In some embodiments, the first medical image may be displayed to the user and the user may select a region of interest, using a user input device such as a mouse or touch screen. In embodiments where the first and second medical images comprise three-dimensional images, the region of interest may comprise a volume (referred to herein as "a volume of interest"). In this way, a user may indicate a portion or region of the full first medical image for which they require synthetic images to be generated. E.g. allowing the user to generate synthetic images of regions of interest precisely and efficiently from larger images.

In some embodiments, image segmentation may be further used to augment this further. For example, in some embodiments, the set of instructions, when executed by the processor, further cause the processor to segment the first medical image to produce a segmentation. In such embodiments, in block iii), the processor being caused to create the synthetic image may comprise the processor being caused to apply the weighted elastic deformation to a portion of the first medical image comprising a region of interest, based on the segmentation.

For example, the processor may determine the location of the region of interest from the segmentation. For example, the user may indicate (in a first user input) a region of the body such as, for example, "thoracic region". In block iii), the synthetic medical image may be created by weighting the determined elastic deformation and applying the weighted elastic deformation to a portion of the first medical image labelled as a thoracic region in the segmentation.

In some embodiments, the region of interest comprises an anatomical feature and the first user input comprises an indication of said anatomical feature. In block iii), the synthetic medical image may be created by weighting the determined elastic deformation and applying the weighted elastic deformation to a portion of the first medical image comprising the anatomical feature (indicated in the first user input), as determined by the segmentation.

In this manner, a user may specify a particular anatomical feature and create synthetic images of said anatomical feature in an efficient manner The skilled person will be familiar with image segmentation, but briefly, image segmentation involves extracting shape/form information about the objects or shapes captured in an image. This may be achieved by converting the image into constituent blocks or "segments", the pixels or voxels in each segment having a common attribute. In some methods, image segmentation may comprise fitting a model to one or more features in an image.

One method of image segmentation is Model-Based Segmentation (MBS), whereby a triangulated mesh of a target structure (such as, for example, a heart, brain, lung etc.) is adapted in an iterative fashion to features in an image. Segmentation models typically encode population-based appearance features and shape information. Such information describes permitted shape variations based on real-life shapes of the target structure in members of the population. Shape variations may be encoded, for example, in the form of Eigenmodes which describe the manner in which changes to one part of a model are constrained, or dependent, on the shapes of other parts of a model. Model-based segmentation has been used in various applications to segment one or multiple target organs from medical images, see for example, the paper by Ecabert, O., et al. 2008 entitled "*Automatic Model-Based Segmentation of the Heart in CT Images*"; IEEE Trans. Med. Imaging 27 (9), 1189-1201.

Another segmentation method uses machine learning (ML) models to convert an image into a plurality of constituent shapes (e.g. block shapes or block volumes), based on similar pixel/voxel values and image gradients.

The skilled person will appreciate however that these are merely examples and that any segmentation method may be used on the first and/or second medical images. As described above, the segmentation may be used to identify regions or anatomical features of interest in order to select an appropriate region or portion of the full first medical image from which to create the synthetic image.

There is thus provided an apparatus for creating synthetic medical images in an efficient manner that enables a user to create synthetic images of particular regions or anatomical features of interest, for a particular demographic of individuals.

Figure 2:
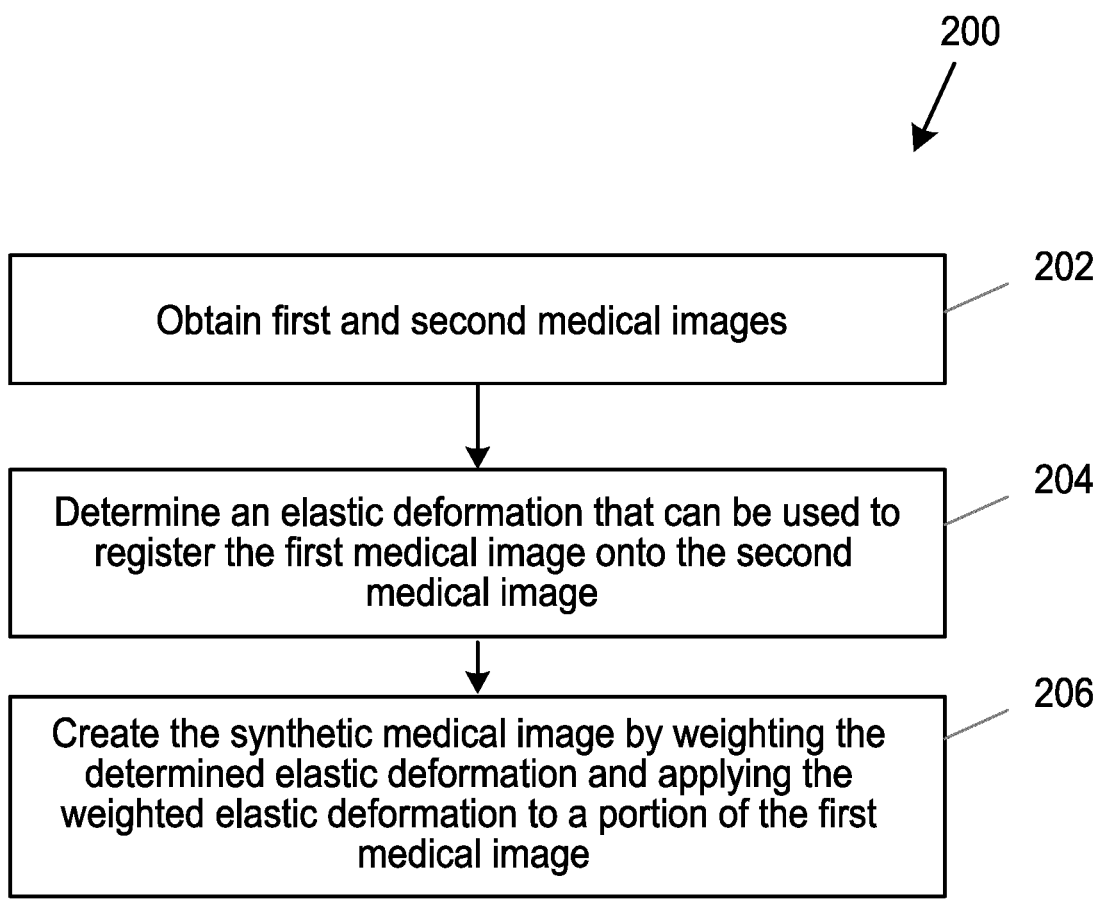
FIG. 2 illustrates a method according to some embodiments herein.

Turning now to another embodiment, as shown in FIG. 2, in some embodiments, there is a method 200 for creating a synthetic medical image. The method 200 may be performed by an apparatus or system such as the apparatus 100. The method 200 may also be performed by one or more blocks of a computer program.

Briefly, in a first step 202 the method comprises obtaining first and second medical images. In a second step 204 the method comprises determining an elastic deformation that can be used to register the first medical image onto the second medical image. In a step 206 the method comprises creating the synthetic medical image by weighting the determined elastic deformation and applying the weighted elastic deformation to a portion of the first medical image.

Obtaining first and second medical images was discussed in detail with respect to block i) performed by the apparatus 100 of FIG. 1 and the detail therein will be understood to apply equally to step 202 of the method 200. Determining an elastic deformation that can be used to register the first medical image onto the second medical image was described above with respect to block ii) performed by the apparatus 100 of FIG. 1 and the detail therein will be understood to apply equally to step 204 of the method 200. Creating a synthetic medical image by weighting the determined elastic deformation and applying the weighted elastic deformation to a portion of the first medical image was described above with respect to block iii) performed by the apparatus 100 of FIG. 1 and the detail therein will be understood to apply equally to step 206 of the method 200.

Figure 3:
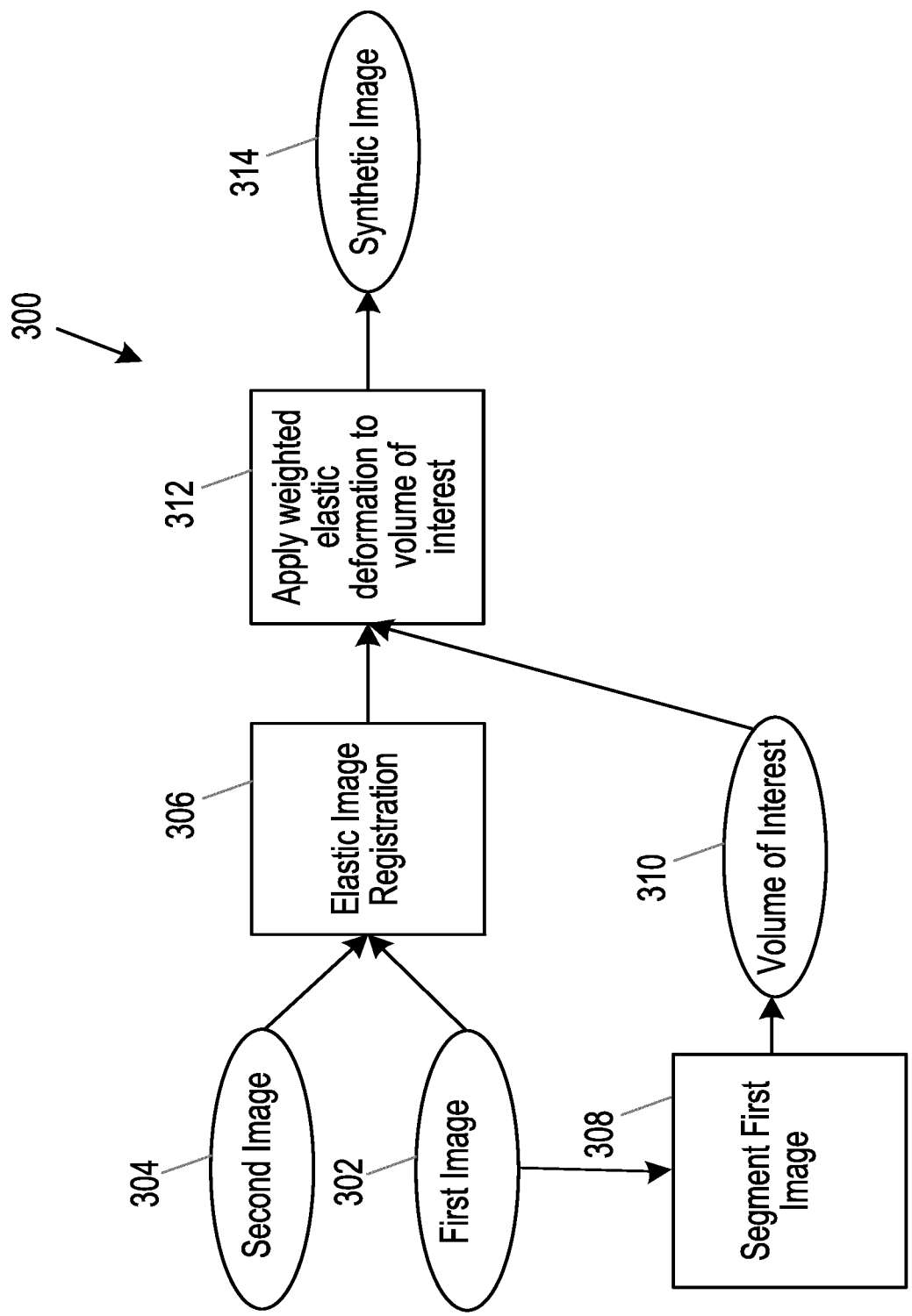
FIG. 3 illustrates another method according to some embodiments herein.

Turning now to FIG. 3, which illustrates a method 300 implemented by an apparatus such as the apparatus 100 according to some embodiments. In this embodiment, first and second medical images 302, 304 are obtained. The first and second medical images are selected so that they match a gender, age and region (or zone) of the body, as indicated by a user in a user input from a user input device 106. The first and second medical images are provided as input to a first module (e.g. first computer module) 306 which determines an elastic deformation that can be used to register the first medical image onto the second medical image.

A second module 308 segments the first medical image to produce a segmentation. The segmentation may be performed using any segmentation method, as described above. The segmentation is used to determine a region or volume of interest (depending on whether the first and second medical images are two-dimensional or three-dimensional respectively) in the first medical image. The region or volume of interest may be determined based on the segmentation and a user input indicating desired region or volume of interest (e.g. a region or volume specified by the user in a user input may be located in the image using the segmentation). A third module 312 creates the synthetic medical image 314 by weighting the determined elastic deformation and applying the weighted elastic deformation to the volume of interest 310 in the first medical image. The volume of interest can be chosen based on the needs from the synthetic data and can include the entire image. In this way, a user can input parameters such as age, gender and an anatomical region or feature and quickly and reliably create synthetic images matching said input parameters.

Turning now to other embodiments, in another embodiment, there is provided a computer program product comprising a computer readable medium, the computer readable medium having computer readable code embodied therein, the computer readable code being configured such that, on execution by a suitable computer or processor, the computer or processor is caused to perform the method or methods described herein. Such as the method 200 or the method 300.

Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or apparatus may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at nm-time. The main program contains at least one call to at least one of the sub-routines. The sub-routines may also comprise function calls to each other.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for creating a synthetic medical image, the apparatus comprising:
    a memory comprising instruction data representing a set of instructions; and
    a processor configured to communicate with the memory and to execute the set of instructions, wherein the set of instructions, when executed by the processor, cause the processor to:
        obtain first and second medical images, wherein the first and second medical images comprise common or overlapping features;
        determine an elastic deformation that can be used to register the first medical image onto the second medical image; and
        create the synthetic medical image by weighting the determined elastic deformation and applying the weighted elastic deformation to a portion of the first medical image so as to create an image having features that are geometrically between the first and second medical images.

2. The apparatus of claim 1, wherein the set of instructions, when executed by the processor, further cause the processor to:
    segment the first medical image to produce a segmentation; and
    wherein the processor further being caused to:
    apply the weighted elastic deformation to the portion of the first medical image comprising a region of interest, based on the segmentation.

3. The apparatus of claim 2, wherein the apparatus is configured to receive a first user input
    indicating the region of interest; and
    wherein the set of instructions, when executed by the processor, cause the processor to perform the obtain, determine, and create responsive to receiving the first user input.

4. The apparatus of claim 3, wherein the region of interest comprises an anatomical feature and the first user input comprises an indication of said anatomical feature.

5. The apparatus of claim 3, wherein the first and second medical images comprise three-dimensional images and the first user input comprises an indication of a volume of interest in the first medical image.

6. The apparatus of claim 1, wherein the weighting is user configurable.

7. The apparatus of claim 6, wherein the apparatus is configured to receive a second user input comprising a value for the weighting.

8. The apparatus of claim 1, wherein the first medical image and the second medical image comprise medical images of human subjects.

9. The apparatus of claim 8, wherein the apparatus is configured to receive a third user input, indicating one or more demographic criteria; and
    wherein the processor further being caused to: select at least one of the first medical image or second medical image from a database of images, based on demographics of respective human subjects in the database of images and the demographic criteria.

10. The apparatus of claim 9, wherein the one or more demographic criteria comprises an age or gender.

11. The apparatus of claim 1, wherein the set of instructions, when executed by the processor, further cause the processor to: repeat the create of the synthetic medical image for a plurality of different weightings to create a plurality of different synthetic medical images.

12. The apparatus of claim 1, wherein the first and second medical images are of a same imaging modality.

13. The apparatus of claim 1, wherein the elastic deformation comprises at least one of a distortion field or the weighting, w, the weighting comprising a value within the interval $0<w<1$.

14. A method of creating a synthetic medical image, the method comprising:

obtaining first and second medical images, wherein the first and second medical images comprise common or overlapping features;

determining an elastic deformation that can be used to register the first medical image onto the second medical image; and creating the synthetic medical image by weighting the determined elastic deformation and applying the weighted elastic deformation to a portion of the first medical image so as to create an image having features that are geometrically between the first and second medical images.

15. A computer program product comprising a non-transitory computer readable medium, the non-transitory computer readable medium having computer readable code embodied therein, the computer readable code being configured such that, on execution by a suitable computer or processor, the computer or processor is caused to:

obtain first and second medical images, wherein the first and second medical images comprise common or overlapping features;

determine an elastic deformation that can be used to register the first medical image onto the second medical image; and create the synthetic medical image by weighting the determined elastic deformation and applying the weighted elastic deformation to a portion of the first medical image so as to create an image having features that are geometrically between the first and second medical images.

* * * * *